United States Patent [19]

Bechara et al.

[11] 4,086,213

[45] Apr. 25, 1978

[54] TERTIARY AMINO ACID AND TERTIARY AMINO ACID-NITRILE DELAYED ACTION CATALYST COMPOSITIONS

[75] Inventors: Ibrahim S. Bechara, Boothwyn;
Philip J. Zaluska, Glen Riddle;
Rocco L. Mascioli, Media, all of Pa.

[73] Assignee: Air Products and Chemicals, Inc., Allentown, Pa.

[21] Appl. No.: 717,579

[22] Filed: Aug. 26, 1976

[51] Int. Cl.$^2$ ............................................. C08G 18/18
[52] U.S. Cl. ..................... 260/77.5 AB; 260/2.5 AB; 260/2.5 AC; 260/75 NB; 260/75 NC; 260/77.5 AC
[58] Field of Search ................... 260/2.5 AB, 2.5 AC, 260/75 NB, 75 NC, 77.5 AB, 77.5 AC

[56] References Cited

U.S. PATENT DOCUMENTS

| | | | |
|---|---|---|---|
| 2,950,262 | 8/1960 | Bush et al. | 260/2.5 AC |
| 3,821,131 | 6/1974 | Priest et al. | 260/77.5 AC |
| 3,862,150 | 1/1975 | Bechara et al. | 260/77.5 AC |
| 3,925,268 | 12/1975 | Rosemund et al. | 260/77.5 AC |

*Primary Examiner*—Eugene C. Rzucidlo
*Attorney, Agent, or Firm*—Russell L. Brewer; Barry Moyerman

[57] ABSTRACT

Tertiary amino acid and tertiary amino acid-nitrile compositions have been found to be effective as delayed action catalysts for polyurethane synthesis. They are particularly effective when used in combination with an organometallic such as an organo tin composition. These compositions generally comprise the reaction product of a primary or secondary amine, an aldehyde and disubstituted acid.

11 Claims, No Drawings

TERTIARY AMINO ACID AND TERTIARY AMINO ACID-NITRILE DELAYED ACTION CATALYST COMPOSITIONS

BACKGROUND OF THE INVENTION

Polyurethanes, which are formed by reacting an isocyanate with a reactive hydrogen providing component, such as a polyol, have been widely used in preparing rigid and flexible foams, castings, adhesives and coatings. Typically, the reaction between the isocyanate and the polyol has been catalyzed by using various components such as amines, e.g. tertiary amines and organometallics, particularly organo tin compounds such as stannous octoate, dibutyl tin laurate, tin ethylhexanoate and so forth. The effectiveness of the catalyst is often measured by the cream time, which is the time required for the isocyanate and polyol syrup to turn from a clear solution to a creamy color; the gel time, which is the time required for polymer particles to form in the syrup; rise time, which is the time required for the syrup to rise to its maximum height; and cure time which is the time to reach a tack-free state.

In some applications for polyurethanes it is desirable to effect reaction in the shortest time possible and, therefore, catalysts having tremendous activity are desired. In some applications, though, as in the molding of intricate parts or large objects, it may be desirable to keep the polyurethane composition in a fluid state for an extended time to permit the composition to fill the mold or flow into the cracks and crevices of the mold. Then, once the mold is completely filled, it is desirable to effect polymerization of the polyurethane in the shortest time possible so that the finished parts can be removed and the mold recharged with new materials. In this regard, it is desirable to delay the initial reaction, but after reaction commences then catalyze the polymerization rate. To do this it is necessary to extend the cream time to permit the polyurethane composition to penetrate the cracks and crevices in the mold and to extend the gelation time as the polyurethane foam gelling becomes intractable and resists molding. However, once the reaction begins, it is desirable to end up with a rise and cure time comparable to those achieved by active catalysts as this will permit greater productivity.

DESCRIPTION OF THE PRIOR ART

Organometallics and particularly organo tin compounds such as tin ethylhexanoate, tin isooctoate, tin naphthenate, di-n-butyl tin dilaurate; dibutyl tin diacetate, and tertiary nitrogen tin compounds such as dibutyl-tin-di(pyridine-4-carboxylic acid esters) as shown in U.S. Pat. Nos. 3,595,734; and 3,164,557 have been used to catalyze urethane reactions.

Amine compounds and particularly tertiary amines or their salts have been used as catalysts for polyurethanes. Examples of amines which are suited for catalyzing polyurethane reactions are dimethyl benzylamine, triethylamine diamine, trimethylamine; alkanolamines such as diethanolamine, triethanolamine, N-diethyl-ethanolamine; N-hydroxy alkyl substituted imidazoles and N-vinyl pyrrolidone as shown in U.S. Pat. Nos. 3,645,927; 3,450,648; 3,448,065 and 3,746,663.

More recently beta-amino carbonyl catalysts and beta-amino nitriles, as described in U.S. Pat. Nos. 3,821,131 and 3,925,268, have been shown as effective catalysts for preparing polyurethanes. Examples of beta-amino carbonyl catalysts include dialkylamino esters such as methyl 3-(N, N-dimethyl amino) proprionate, dialkylaminoamide, e.g. diethylamino-N,N-diethylproprionamide and beta-amino nitriles such as 3-(N-morpholino)-2-methyl-N'N'-dimethyl amino proprionitrile, 1,4-piperizine diproprionitrile, and N-ethyl-N-(2 cyanoethyl) amine. These catalysts also have an advantage in that the resulting product does not have the characteristic amine odor.

U.S. Pat. Nos. 3,620,986 and 3,580,868 show that Mannich bases of secondary amines and phenols can be used for catalyzing an ixocyanate-hydroxyl reaction. Generally, some aminoalcohol is present and the phenol radical may contain an active hydrogen atom, e.g. COOH, $CONH_2$, OH, etc., which can condense into the urethane structure. Typically, these Mannich bases are formed by reacting dimethylamine, formaldehyde, aminoalcohol and a phenol, e.g. Bisphenol A, or salicyclic acid amide.

Although the above references indicate the compositions have catalytic activity, a number of references have suggested similar but different compositions as being useful as delayed action catalysts (DAC), i.e. those which initially delay and then catalyze the isocyanate-hydroxyl reaction. For example, chelating agents, e.g. beta-diketones and beta-carbonyls with amine-free organometallics have been used. Examples of beta-diketones useful as a delayed action catalyst in polyurethane chemistry include 2,4-hexanedione, acetylacetone, 1,cyclohexyl-1, 3 butanedione; beta-hydroxy ketones, e.g. beta-hydroxy quinoline, 1-hydroxy-9-fluorenone, and alpha-hydroxy ketones, e.g. benzoin, acetoin and others as shown in U.S. Pat. No. 3,635,906.

Another example of a delayed action catalyst for the preparation of foamed polyurethane resins is shown in U.S. Pat. No. 2,932,621. This patent discloses that amine salts of dicarboxylic acids and notably the hydroxy tertiary amine salts of oxalic acid are particularly effective in delaying the initial reaction between an isocyanate and hydroxyl group, but after an appropriate lapse of time, they become fully effective and cause the reaction to proceed to completion smoothly, rapidly and efficiently.

It has also been proposed to use quaternary ammonium salts of Mannich bases as a delayed action catalyst for the reaction between an isocyanate and polyol to form polyurethanes. Generally the quaternary ammonium salt has little initial catalytic effect, but during the reaction it decomposes to form a tertiary amine which can catalyze the reaction. Examples of quaternary ammonium salts of Mannich bases are shown in U.S. Pat. No. 2,950,262 and are prepared by reacting a secondary amine with an aldehyde and a ketone such as cyclohexanone and then reacting the Mannich base with an organic halide to form the quaternary ammonium salt. This catalyst is not particularly effective as a delayed action catalyst when used in conjunction with organometallics.

It has also been proposed to sorb conventional polyurethane catalysts such as tertiary amines or organometallics onto an organic support having a density of from about 0.01 to about 0.6 $g/cm^3$ in order to delay their activity. Examples of organic supports which are used in forming the delayed action catalysts are polymethyl methacrylate, polystyrene, polyvinyl acetate, polyvinyl chloride, and copolymers thereof. Further examples are set forth in U.S. Pat. No 3,136,731.

Some of the problems with delayed action catalysts (DAC) in the past have been that not only did they delay cream time and gelation time, but also they delayed the rise and cure time. As a result, these DAC's resulted in lower production rates.

SUMMARY OF THE INVENTION

This invention relates to polyurethane compositions containing a catalyst comprising a tertiary amino acid or tertiary amino acid-nitrile, preferably in combination with an organometallic, and to a method for catalyzing the reaction between an isocyanate and a compound having a reactive hydrogen atom, as determined by the Zerewitinoff method, to form polyurethanes.

The catalysts of this invention have the ability, particularly when combined with other catalytic components, e.g. organometallics such as organo tin compositions, to delay the initiation of the isocyanate reaction thereby extending the cream and gelation time and yet catalyze the reaction to give a cure time which is essentially the same as would be achieved if the organometallic or other catalytic component were used alone.

Broadly, the delayed action catalyst composition comprises an acid or acid nitrile substituted amine represented by the formula:

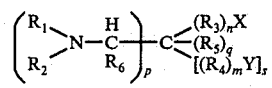

wherein R and $R_2$ independently are hydrogen and only one is hydrogen at a time) alkyl and substituted alkyl groups having from 1 to 15 carbon atoms, or are combined to form a piperidine, piperizine, morpholino, imidazolo or imidazolino radical;

wherein $R_3$ and $R_4$ independently are alkylene groups having from 1-2 carbon atoms, aralkylene with the alkylene portion having from 1 to 6 carbon atoms, substituted alkylene and substituted aralkylene groups;

wherein $R_5$ independently is hydrogen, a lower alkyl group having from 1 to 6 carbon atoms, an alkenyl group having from 2 to 6 carbon atoms, an aryl group and substituted derivatives, a cyclic group and substituted derivative thereof, or a keto alkyl group with the alkyl portion having from 1-6 carbon atoms;

wherein $R_6$ independently is hydrogen, or a radical selected from the group consisting of alkyl, phenyl, furfuryl, naphthyl, and substituted derivatives of such groups;

wherein X independently is a carboxylic acid group or a quaternary ammonium salt of an acid group;

wherein Y independently is a carboxylic acid group, nitrile group, or a quaternary ammonium salt of an acid group; and, wherein $m$ and $n$ independently are 0 or 1;
wherein $q$ independently is 0 or 1.
wherein $p$ independently is 1 or 2; and
wherein $s$ independently is 0 or 1; and
wherein $p + q + s$ is 3.

Advantages of the catalyst of this invention include: the ability to delay the initial reaction between an isocyanate and an active hydrogen containing compound in the formation of a polyurethane; the ability to form a polyurethane having excellent flow during initial cure by extending the cream and gelation time and yet ending up with a desirable rise and cure time which is comparable to conventional catalyst compositions;

the ability to form polyurethane compositions containing tertiary amino compositions which are substantially free of the characteristic amine odor found heretofore;

the ability to delay amine and organometallic catalyzed urethane polymerization; and the ability to form thermally sensitive tertiary amine salts of tertiary amino acids which decompose on heating to generate additional tertiary amine or catalysis.

DESCRIPTION OF THE PREFERRED EMBODIMENTS

Broadly, the tertiary amino acid and tertiary amino acid-nitrile delayed action catalysts (DAC's) of this invention can be visualized as Mannich adducts having at least monofunctionality in terms of tertiary amine and at least monofunctionality and preferably difunctionality in the form of acid and nitrile. The Mannich adducts are formed by reacting a primary or secondary amine with an aldehyde and an organic compound having a hydrogen atom sufficiently active to undergo a Mannich condensation and having pendant acid or nitrile functionality or functionality which can be subsequently converted to the acid or nitrile.

Primary and secondary amines generally can be used in forming Mannich Adducts although secondary amines are preferred as the resulting compound is less complex. The primary or secondary amines can be aliphatic, or ring compounds including heterocyclic rings, In the preferred embodiment, secondary hydroxyalkyl amines having from 2 to 15 carbon atoms, and generally from 2 to 4 carbon atoms are employed. Example of primary and secondary amines suited for forming the Mannich Adduct include methylamine, ethylamine, dimethylamine, diethylamine, diethanolamine, dipropanolamine, piperidine, piperizine, imidazole, morpholine, and the like. Furthermore, the amines can be substituted with inert groups without detracting from the effectiveness of the adduct as a delayed action catalyst. By inert groups it is meant that the substituent groups should not be reactive with the aldehyde or organic compound having the active hydrogen atom as it would inherently interfere with the formation of the appropriate Mannich Adducts. Examples of inert substituted groups include pendant alkyl, alkoxy, ether and hydroxyl groups.

The second component used in forming the Mannich adduct is an aldehyde. Aldehydes and substituted aldehydes useful in forming the Mannich adducts are well known and can be used here. As taught in the art, these aldehydes must have a pendant aldehyde group which is sufficiently reactive to form the Mannich Adduct. Typically, these aldehydes are activated as for example, by an unsaturated group in conjugated relationship with the carbonyl aldehyde. Examples of aldehydes best suited for practicing the invention are formaldehyde, benzaldehyde, furfuraldehyde, naphthaldehyde, and substituted aldehydes such as nitrobenzaldehyde, nitrofurfural, cyanofurfuraldehyde and the like. For reasons of efficiency and economy, formaldehyde, benzaldehyde an furfuraldehydes are the preferred aldehydes used in forming the adduct.

The remaining component necessary for forming the Mannich adduct is an organic compound having at least one hydrogen atom sufficiently reactive for undergoing a Mannich reaction. Generally in such compounds, the hydrogen atom is positioned on a methylene group alpha positioned to a carbonyl group such as a ketone, a carboxylic acid ester or an acid group. Further, the organic compound should have a pendant carboxylic acid or nitrile group or a structure, e.g. ketone and ester permitting the substitution or addition of a carboxylic acid or nitrile group. Examples of organic compounds having at least one active hydrogen atom and in some instances, two active hydrogen atoms suited for practicing the invention include disubstituted saturated acids such as malonic acid, benzyl malonic acid, lower alkyl ($C_1$-$C_3$) malonic acids, furfuryl malonic acid, alkenyl malonic acids, e.g. allyl malonic acid; p-nitrophenylacetic; p-nitrophenyl glycolic acid; ethane-tricarboxylic acid; cyanoacetic acid and ketoacids, e.g. acetone dicarboxylic, levulinic and pyruvic acids.

Of the compounds listed as being suited for practicing the invention, some are more difficult to synthesize than others primarily because of lesser activity of the hydrogen atoms. For example, levulinic is much more difficult to react than malonic acid and yet in terms of acid functionality introduced, the result is the same. What is intended by this listing is to show that a variety of amines, aldehydes and organic compounds and that a variety of amines, aldehydes and organic compounds and substituted amines, aldehydes and organic compounds can be used to form a Mannich Adduct that can be used as a delayed action catalyst in the practice of this invention.

Quaternary ammonium salts (which, be definition herein, include amine salts) of the acid substituted adducts can be formed and used as delayed action catalysts. Generally, the quaternary ammonium functionality detracts from the delayed action of the catalyst vis-a-vis an organometallic catalyst as the acid or nitrile functionality is more effective in tieing the metal portion than the quaternary ammonium salt. On the other hand, the increased amine content, which results on decomposition of the quaternary ammonium salt, can enhance the catalytic activity and reduce the rise and cure time. Although a cream time slightly less than the cream time for an organometallic catalyzed polyurethane may be observed for some tertiary amine salts of DAC's, the cream time is substantially longer than if the DAC were not present. For example, a tertiary amine-organometallic catalyzed reaction will have a much shorter cream time than the same urethane composition catalyzed with similar quantities of amine and organometallic, but including a DAC, i.e., the teritiary amino acid. Quaternary ammonium salts can be formed by reacting the acid substituted adducts with amines such as ethanolamine, dimethyl amine and tertiary amines, triethylenediamine, diethylenetriamine, trimethylamine, quinuclidine and a hydroxy substituted tertiary amine such as triethanolamine. The formation of quaternary ammonium salts of the acid Mannich Adducts can also serve a second purpose in that it often enhances the solubility of the delayed action catalyst in the polyurethane syrup as will be explained.

Often where a plurality of acid groups are present and the organo portion of the Mannich adduct is relatively small or negated by the fact that a hydroxyl or other polar group is present, it may be necessary to use a solvent to disperse the delayed action catalyst in the syrup. Virtually any solvent may be used which does not compete with the isocyanate-active hydrogen to form a polyurethane, and which does not impart adverse effects to the resultant polyurethane can be used. Conventional solvents such as glycols, e.g. propylene glycol, ethylene glycol, dipropylene glycol, polar solvents such as dimethyl formamide; ethylene carbonate, amines (which form salts with the acid group) and other solvents ae used. Amino-nitrile compositions such as cyanoethyldiethanolamine, which is also a catalyst, can also be used as a solvent. Solvent selection is well within the skill of those in the art.

The second component generally used in forming a preferred urethane catalyst of this invention is a conventional organometallic used for the catalysis of polyurethanes. Typically, these organometallics have the formula $R_nM$ wherein R designates the organo moiety, M represents the metallic moiety and $n$ is an integer sufficient to satisfy the valence of the metal component. Generally, the metals in the organometallic include antimony, tin, lead, manganese, mercury, cobalt, nickel, iron, vanadium and copper. From a commercial point of view, only a few of these metals are used in polyurethane synthesis as they have advantages of cost and they do not affect product quality. For example, iron, although it is effective for catalyzing the isocyanate-hydroxyl reaction, may cause discoloration. Of the metals listed, tin is probably the metal that is used in greatest proportion, and it is preferred in practicing this invention.

The organo portion of the organometallic component is present to provide solubility of the metal in the isocyanate syrup. The solubility of the organometallic should be at least about 1 gram per 100 grams of syrup at 50° C and organo portions which provide the solubility are operable. Generally, the organo portion is an alkyl group having from 4-15 carbon atoms or an alkoxy group, although cyclic and cycloaliphatic groups can be used. Examples of organometallics suited for practicing this invention include dibutyl tin dilaurate, dibutyl tin diacetate, diethyl tin diacetate, dihexyl tin diacetate, dibutyl tin-di(2 ethyl hexanoate), stannous octoate, tin decanoate, di-N-octyl tin mercaptide, iron acetylacetonate, dioctyl tin oxide, dimethyl tin oxide, titanium acetyl acetonate, and so forth. Other examples are set forth in numerous U.S. patents, e.g. 3,595,734; 3,164,557 and 3,925,268; and are incorporated by reference.

Although not intending to be bound by theory, it is believed an acid, a nitrile, a second tertiary amino group, or a hydroxyl group to some extent when coupled to a tertiary amine nitrogen as in the Mannich adducts of the invention ties the metal portion of an organometallic catalyst or ties a tertiary amine catalyst during the initial part of the isocyanate-active hydrogen compound reaction thereby diminishing its catalytic activity. Accordingly, as the number of substituent acid groups are increased on the Mannich adduct moiety, as for example in a disubstituted moiety, the greater the chelating or tieing effect. (Although trisubstituted and tetrasubstituted acid Mannich Adducts provide an even greater tieing of organometallic and tertiary amine and diminish initial activity, they are difficult to disperse in th polyurethane syrup.) As the isocyanate reaction begins and the temperature of reaction increases, the acid functionality of the Mannich adduct loses its ability to tie the metal or amine and releases the metal or amine. On release, the metal or amine catalyzes the isocyanate reaction. However, not only does the Mannich Adduct release the metal or amine (where the salt is formed), the tertiary amino portion of the Mannich Adduct then acts as a catalyst in combination with the organometallic or amine to promote the reaction. In this way, the catalysts exhibit initial delay in the reaction without substantially sacrificing overall cure time and product quality.

Any polyisocyanate suited for forming polyurethanes is suited for practicing this invention. Representative polyisocyanates suited for producing polyurethanes and practicing this invention are the aliphatic and aromatic polyvalent isocyanates. Examples of aliphatic isocyanates include alkylene diisocyanates such as tri, tetra and hexamethylene diisocyanates; arylene diisocyanates and their alkylation products such as phenylene diisocyanate, naphthylene diisocyanate, diphenylmethane diisocyanate, toluene diisocyanate, di and triisopropyl benzene diisocyanate and triphenylmethane triisocyanates, triesters of isocyanato phenyl-thiophosphoric acid; triesters of para-isocyanato phenyl phosphoric acid; aralkyl diisocyanates such as 1-(isocyanatophenolethyl) isocyanate or xylene diisocyanate.

Any polyol suited for forming polyurethanes can be used in practicing this invention. Examples of polyols include aliphatic polyether polyols prepared from the reaction of ethylene or propylene oxides or mixtures thereof with a glycol; glycols such as ethylene glycol, propylene glycol, butylene glycol, tetramethylene glycol, hexamethylene glycol, and triols such as glycerol, trimethylolpropane, trimethylol ethane, and higher polyols such as pentaerythritol, sorbitol, castor oil, polyvinyl alcohol, sucrose, dextrose, methyl glycoside and the like; amino polyols made by the condensation of alkylene oxides and alkanol amines such as tetrahydroxyethylene diamine, tetrahydroxypropyl ethylene diamine; other organic compounds having an active hydrogen atom are amines such as triethanolamine, methylamine, diethanolamine, phenylenediamine, tolylene diamine, piperizine and the like.

The polyols also can be incorporated into a polymer and reacted with the isocyanates as in the case of polyesters. A polyester, as is known, is prepared by the reaction between a dicarboxylic acid and a glycol. Examples of conventional dicarboxylic acids suited for manufacturing polyester polyols include succinic, glutaric, adipic, sebacic, phthallic, terephthallic, maleic, fumaric, itaconic, citraconic, and the like.

In the preparation of polyurethanes, conventional additives can be utilized for their desired effect without departing or detracting from the advantageous aspects of the catalysts of this invention. For example, blowing agents such as water or a volatile organic such as dichlorodifluoromethane, dichlorofluoromethane, trichloromonofluoromethane, dichlorofluoromethane, difluorodichloroethane, methylene chloride, carbontetrachloride, butane, pentane, and the like.

Foam stabilizers or surfactants are another additive which can be added for enhancing the retention of gas generated during the polymerization reaction and such stabilizers include silicone block polymers comprising polyalkylene glycol units, n-vinyl pyrrolidone, or n-vinyl pyrrolidone-dibutyl maleic copolymers or n-vinyl pyrrolidone-dibutyl maleate (vinyl acetate). Other examples are shown in U.S. Pat. No. 3,746,663.

In preparing the polyurethanes, the tertiary amino acid or nitrile (DAC) is added to the urethane composition in at least a sufficient or effective proportion for enhancing the cure rate of the polyurethane. When the DAC is used alone, generally from about 0.1 to about 5 parts by weight per 100 parts and preferably about 0.5 to about 1.5 per 100 parts by weight of reactive Zerewitinoff hydrogen compound, e.g. polyol, are included. When less than about 0.1 parts are added to the composition, the DAC is not present in sufficient proportion to influence substantially the cure rate of the polyurethane. When more than about 5 parts amino acid are added to the urethane composition, no significant advantage in terms of increased cure rate is achieved. For reasons of economy, the catalyst concentration is preferably from about 0.5 to about 1.5 parts.

Conventionally, organometallic components are included in polyurethene manufacture in a proportion of from about 0.005 to about 0.5, and preferably 0.01 to 0.2 parts by weight per 100 parts of active Zerewitinoff hydrogen compound. Variations within this broad range are found particularly when high and low density polyurethanes are prepared and these variations are observed in practicing this invention. Generally, in formulating high density polyurethanes, from about 0.03 to about 0.07 parts organometallic, e.g. organo tin, compound are used. In formulating low density polyurethanes from about 0.08 to about 0.2 parts organometallic compound are used. Naturally, as the proportion of organometallic compound is increased in the urethane composition, the proportion of amino acid or nitrile should be increased if one wants to delay substantially the urethane reaction or inhibit other adverse effects of the organometallic catalyst. However, the formulator can adjust the concentration of organometallic and amino acid or amino acid-nitrile as desired within the above range to achieve desired conditions for his line of products.

In visualizing the tertiary amino acid and the organometallic as a catalyst composition for urethane catalysis, approximately from about 0.1 to about 100 parts tertiary amino acid (DAC) are present per part of organometallic. Preferably, the catalyst composition comprises preferably 0.6–60, and most preferably from about 2 to about 20 parts tertiary amino acid per part organometallic. Thus, when the catalyst composition comprising the tertiary amino acid and organometallic are combined in suitable proportion for catalyzing the urethane reaction, then both components of the catalyst will be present in the reaction mixture in the desired range to achieve desired results. When less than about 0.1 part tertiary amino acid are included per part of organometallic catalyst, and the catalyst composition is added to the urethane composition, then there generally is insufficient tertiary amino acid in the urethane composition to counteract the catalyst activity of the organometallic or adverse effect of the organometallic. On the other hand, as the proportion of tertiary amino acid is increased above 20 parts/part organometallic catalyst, the benefits become less distinctive. When levels above 100 parts/part organometallic catalyst are employed, no significant enhancement of catalytic activity or of other desired features in the urethane composition are observed to warrant the additional expenditure and usage of the catalyst.

The following examples are provided to illustrate preferred embodiments of this invention and are not intended to restrict the scope thereof. All parts are parts by weight and all percentages are weight percentages.

EXAMPLE 1

Bis(morpholinomethyl)-acetic acid was prepared conventionally in a flask equipped with a stirrer and reflux condenser by first changing 0.1 moles of malonic acid, 0.2 moles morpholine, and 100 cc water. The contents were warmed to a temperature of about 20° C and then 0.2 moles formaldehyde as a 40% aqueous solution were added to the flask and the reaction commenced. When the evolution of carbon dioxide ceased, the water was removed from the reaction mixture by coupling the flask to a vacuum source and heating to a temperature of about 50° C. The syrupy residue remaining in the flask then was triturated in acetone and the resulting white crystalline solid isolated by filtration. The melting point of the product was about 129°–130° C.

EXAMPLES 2 – 12

In the following examples a variety of tertiary amino acids were prepared in accordance with the method of Example 1 except that the various amines, aldehydes, and acids or nitriles listed and proportions thereof were substituted for the respective components in Example 1. The product produced is set forth in Table I.

| Component | Amount, parts by weight |
|---|---|
| DC-193 (silicone surfactant) | 0.8 |
| Tertiary amino acid or nitrile catalyst parts/100 parts polyol (php) | 0.01 – 0.5 |
| Organometallic catalyst parts/100 parts polyol (php) | 0.005 – 0.5 |

(1) Mondur MR Isocyanate is crude 4,4'-methylene bisphenylisocyanate having an isocyanate equivalent of about 133, a functionality of about 2.7–2.9 and a viscosity of about 150–250 cps.

(2) NIAX DAS-361 Polyol is a sucrose/amine polyol having a hydroxyl number of 360.

TABLE I

| EXAMPLE | AMINE | ALDEHYDE | ACID | AMINE | PRODUCT |
|---|---|---|---|---|---|
| Ex. 2 | 0.1 m diethanolamine | 0.1 m formaldehyde | 0.1 m malonic acid | — | bis(hydroxyethyl)amino methyl malonic acid |
| Ex. 3 | 0.2 m diethanolamine | 0.2 m formaldehyde | 0.1 m malonic acid | — | bis[bis hydroxyethyl)amino methyl] acetic acid |
| Ex. 4 | 0.1 m diethanolamine | 0.1 m furfuraldehyde | 0.1 m malonic acid | — | bis(hydroxyethylamino) furfuryl malonic acid |
| Ex. 5 | 0.1 m diethanolamine | 0.1 m benzaldehyde | 0.1 m malonic acid | 0.2 m TEDA | triethylenediamine salt of bis (hydroxyethylamino) benzyl malonic acid) |
| Ex. 6 | 0.1 m morpholine | 0.1 m benzaldehyde | 0.1 m malonic acid | — | morpholino benzyl malonic acid |
| Ex. 7 | 0.2 m piperidine | 0.2 m formaldehyde | 0.1 m malonic acid | — | bis(piperdinylmethyl) acetic acid |
| Ex. 8 | 0.2 m methyl piperazine | 0.2 m formaldehyde | 0.1 m malonic acid | — | bis(methylpiperazinomethyl) acetic acid |
| Ex. 9 | 0.2 m imidazole | 0.2 m formaldehyde | 0.1 m malonic acid | — | bis(imidazolo methyl) acetic acid |
| Ex. 10 | 0.1 m piperidine | 0.1 m formaldehyde | 0.1 m malonic acid | — | piperidinyl methyl malonic acid |
| Ex. 11 | 0.1 m morpholine | 0.1 m benzaldehyde | 0.1 m cyanoacetic | 0.1 m TEDA | triethylene diamine salt of morpholino benzyl cyanoacetic acid |
| Ex. 12 | 0.2 m morpholine | 0.2 m formaldehyde | 0.1 m malonic acid | — | bis(morpholinomethyl) acetic acid |

EXAMPLE 13

Conventional high density rigid polyurethane foams were prepared from the basic formulation below in conventional manner. In preparing these polyurethane foams, the catalyst, comprising an amine or tertiary amino acid (as indicated), and organometallic (as indicated) and the concentration of each catalyst component were varied to determine the overall effect on the foam formulation. The polyurethane foams were evaluated for cream time, gelation time, and cure time.

The components used for preparing the high density foam were as follows:

| Component | Amount, parts by weight |
|---|---|
| Mondur MR® Isocyanate | 100 |
| NIAX® DAS-361 Polyol | 65 |
| Thanol® G-400 Polyol | 27.7 |
| Polylite® 34-400 Polyol | 5.0 |
| Water | 0.6 |

(3) Thanol G-400 Polyol is a glycerol polyol having an hydroxyl number of 400.

(4) Polylite 34-400 Polyol is an amino polyol having a hydroxyl number of 790.

(5) In the examples to follow, TEDA refers to triethylene diamine; DEA refers to diethanolamine; MEA refers to monoethanolamine; EC refers to ethylene carbonate; DPG refers to dipropylene glycol; DMF refers to dimethyl formamide; EG refers to ethylene glycol; PG refers to propylene glycol; T-9 refers to stannous octoate; T-12 refers to dibutyl tin dilaurate; PbAc refers to lead acetate; Co naphthenate refers to cobalt napthenate; MnA refers to manganese acetate; the catalyst referred to by Ex. — corresponds to the product of the Example having the same number; php refers to the total amount of catalyst (including solvent if used) per 100 parts polyol.

The results of the formulation testing is set forth in Tables II through V.

TABLE II

HIGH DENSITY RIGID FOAM

| Catalyst php | Solvent | Organometallic php | Cream Time Sec. | Gel Time Sec. | Tack Free Cure Time Sec. |
|---|---|---|---|---|---|
| TEDA (0.7) | (70% PG) | | 34 | 81 | 106 |
| — | — | T-12 (0.04) | 44 | 78 | 87 |
| TEDA (0.7) | (70% PG) | Lead Acetate (0.04) | 12 | 32 | 43 |
| TEDA (0.7) | (70% PG) | T-12 (0.04) | 29 | 42 | 49 |
| Ex.2 (0.5) | (neat) | T-12 (0.04) | 55 | 98 | 111 |
| Ex.2 (1.0) | (neat) | T-12 (0.04) | 57 | 104 | 120 |
| Ex.2 (1.5) | (neat) | T-12 (0.04) | 57 | 118 | 139 |
| Ex.3 (0.5) | (neat) | T-12 (0.04) | 55 | 98 | 111 |
| Ex.3 (1.0) | (neat) | T-12 (0.04) | 57 | 104 | 120 |
| Ex.3 (1.5) | (neat) | T-12 (0.04) | 57 | 118 | 139 |
| Ex.3 (0.5) | (33% in DPG) | T-12 (0.04) | 58 | 95 | 104 |
| Ex.3 (1.0) | (33% in DPG) | T-12 (0.04) | 59 | 108 | 124 |
| Ex.4 (0.5) | (neat) | T-12 (0.04) | 76 | 118 | 138 |
| Ex.4 (1.0) | (neat) | T-12 (0.04) | 80 | 129 | 150 |
| Ex.4 (0.5) | (neat) | T-12 (0.05) | 68 | 105 | 117 |

TABLE II-continued
HIGH DENSITY RIGID FOAM

| Catalyst php | Solvent | Organometallic php | Cream Time Sec. | Gel Time Sec. | Tack Free Cure Time Sec. |
|---|---|---|---|---|---|
| Ex.4 (1.0) | (neat) | T-12 (0.05) | 75 | 110 | 128 |
| Ex.5 (0.5) | (neat) | — | 61 | 132 | 176 |
| Ex.5 (0.7) | (neat) | — | 53 | 113 | 160 |
| Ex.5 (1.0) | (neat) | — | 44 | 93 | 125 |
| Ex.5 (0.5) | (neat) | T-12 (0.03) | 48 | 77 | 86 |
| Ex.5 (1.0) | (neat) | T-12 (0.03) | 43 | 69 | 79 |
| Ex.5 (0.5) | (neat) | T-12 (0.04) | 46 | 71 | 78 |
| Ex.5 (1.0) | (neat) | T-12 (0.04) | 40 | 64 | 72 |
| Ex.5 (0.5) | (neat) | T-12 (0.05) | 44 | 63 | 69 |
| Ex.5 (1.0) | (neat) | T-12 (0.05) | 37 | 61 | 65 |

TABLE III
HIGH DENSITY RIGID FOAM

| Catalyst php | Solvent | Organometallic php | Cream Time Sec. | Gel Time Sec. | Tack Free Cure Time Sec. |
|---|---|---|---|---|---|
| Ex.6 (0.5) | (33% in DMF) | T-12 (0.03) | 61 | 110 | 132 |
| Ex.6 (0.5) | (33% in DMF) | T-12 (0.04) | 59 | 103 | 124 |
| Ex.6 (1.0) | (33% in DMF) | T-12 (0.04) | 65 | 122 | 153 |
| Ex.6 (0.5) | (33% in DMF) | T-12 (0.05) | 55 | 94 | 110 |
| Ex.2 (0.5) | (33% in DPG) | T-12 (0.04) | 58 | 95 | 104 |
| Ex.2 (1.0) | (33% in DPG) | T-12 (0.04) | 59 | 108 | 124 |
| Ex.7 (0.5) | (33% in ethylene carbonate) | T-12 (0.04) | 48 | 76 | 86 |
| Ex.7 (1.0) | (33% in ethylene carbonate) | T-12 (0.04) | 41 | 71 | 82 |
| Ex.8 (0.5) | (33% in EG) | T-12 (0.04) | 49 | 82 | 91 |
| Ex.8 (1.0) | (33% in EG) | T-12 (0.04) | 49 | 81 | 90 |
| Ex.9 (0.5) | (33% in ethylene carbonate) | T-12 (0.04) | 49 | 97 | 114 |
| Ex.9 (1.0) | (33% in ethylene carbonate) | T-12 (0.04) | 50 | 98 | 116 |
| Ex.10 (0.5) | (33% in ethylene carbonate) | T-12 (0.04) | 54 | 102 | 117 |
| Ex.10 (1.0) | (33% in ethylene carbonate) | T-12 (0.04) | 54 | 121 | 145 |

TABLE IV
HIGH DENSITY RIGID FOAM

| Catalyst php | Solvent | Organometallic php | Cream Time Sec. | Gel Time Sec. | Tack Free Cure Time Sec. |
|---|---|---|---|---|---|
| ethylene diamine (0.4) | — | — | 60 | 197 | >6′ |
| diethanolamine (0.4) | — | — | 68 | 244 | >6 min. |
| diethylene triamine (0.4) | — | — | 59 | 228 | >6 min. |
| dibenzyl amine (0.4) | — | — | 52 | 253 | >6 min. |
| n-butyl amine (0.4) | — | — | 61 | 244 | >6 min. |
| Ex.6 (0.5) | 33% in DMF | T-12 (0.04) | 59 | 103 | 124 |
| Ex.6 (1.0) | 33% in DMF | T-12 (0.04) | 65 | 122 | 153 |
| — | — | T-12 (0.01) | 80 | 147 | 180 |
| Ex.11 (0.5) | (50% DPG) | — | 75 | 157 | 227 |
| Ex.11 (1.5) | (50% DPG) | — | 50 | 107 | 154 |
| Ex.11 (0.5) | (50% DPG) | T-12 (0.01) | 53 | 100 | 125 |
| Ex.11 (1.5) | (50% DPG) | T-12 (0.01) | 43 | 82 | 105 |
| — | — | T-12 (0.03) | 46 | 82 | 94 |
| Ex.11 (1.5) | — | T-12 (0.03) | 33 | 90 | 111 |
| Ex.12 (1.0) | — | T-9 (0.04) | 32 | 78 | 109 |
| — | — | T-9 (0.04) | 26 | 54 | 64 |

In reviewing the results from Tables II–IV, it is readily observed that the tertiary amino acids of this invention act as a delayed action catalyst in that the cream time is extended in virtually every case where the catalyst is added to a tin catalyzed high density polyurethane formulation. Although the tack free or cure time is slightly extended in most cases as compared to an organometallic catalyzed polyurethane composition, the percentage of increase in cream time in the DAC catalyzed polyethane composition generally is higher than the percentage increase in the tack free or cure time. Also, a formulator may not object to the extended cure time as delayed initiation may be of higher priority. Delayed action is also shown in the triethylene diamine salts of the tertiary amino acid over a corresponding triethylene diamine-organo tin catalyzed polyurethane composition thus showing the ability of the delayed action catalyst to tie either the amine or tin, or both, during the initial stages of polymerization.

EXAMPLE 14

Conventional low density rigid polyurethane foam formulations utilizing the components set forth below were prepared in conventional manner. In these polyurethane foams, the catalysts comprising an amino acid and organometallic and the concentration were varied.

The basic formulation used for the low density rigid polyurethane foam was as follows:

| Component | Amount, parts |
|---|---|
| Hylene® TIC[1] | 105 |
| RS-6406 Polyol[2] | 109 |
| DC193[3] Surfactant | 1.5 |
| R11[4] Blowing Agent | 47 |

[1]Hylene TIC is an undistilled, technical grade of tolylene diisocyanate typically having an isocyanate content of 38.75 to 39.75%, an amine equivalent of 105.5 to 108 and a viscosity at 25° C of 15 to 75 cps.
[2]RS-Polyol is a sucrose/amine polyol having a hydroxyl number 475.
[3]DC-193 Surfactants are polysiloxane polyoxyalkylene block copolymers. Examples are shown in U.S. Pat. 2,834,748 and 2,917,480.
[4]R-11 Blowing Agent is trichloromonofluoromethane.
[5]See paragraph (5) of Example 13 for an explanation of additional terms.

to breakdown of the structure. This is not a problem in high density formulations.

EXAMPLE 15

Conventional semi-flexible polyurethane foam formulations were prepared from the components listed below in conventional manner. In these polyurethane foam formulations, the catalyst comprising an aminoacid and organometallic and the concentrations were varied as indicated and the foams evaluated.

| Component | Amount, parts by weight |
|---|---|
| PAPI® 901 Isocyanate[1] | 34 |
| NIAX® 34–28 Polyol[2] | 50 |
| TPE-4542 Polyol[3] | 30 |

TABLE V
LOW DENSITY RIGID FOAM

| Catalyst php | Solvent | Organometallic php | Cream Time Sec. | Gel Time Sec. | Tack Free Cure Time Sec. | Friability | Shrinkage |
|---|---|---|---|---|---|---|---|
| N,N-dimethyl-cyclohexyl amine (0.8) | — | — | 18 | 77 | 168 | None | None |
| — | — | T-12 (0.08) | 36 | 107 | 184 | Moderate-Severe | Moderate-Severe |
| — | — | T-12 (0.10) | 32 | 91 | 137 | Moderate | Moderate |
| — | — | T-12 (0.15) | 27 | 78 | 111 | Slight-Moderate | Slight-Moderate |
| — | — | T-12 (0.20) | 23 | 57 | 93 | Slight | Slight |
| N-dimethyl-cyclohexyl amine (0.8) | — | T-12 (0.06) | 15 | 68 | 105 | None | None |
| " | — | T-12 (0.08) | 14 | 55 | 94 | None | None |
| Ex.2 (0.5) | (64% in DPG) | T-12 (0.08) | 40 | 137 | 241 | Very slight | Very slight |
| Ex.2 (1.0) | (64% in DPG) | T-12 (0.08) | 38 | 140 | 251 | None | None |
| Ex.2 (0.5) | (64% in DPG) | T-12 (0.1) | 39 | 133 | 216 | None | None |
| Ex.2 (1.0) | (64% in DPG) | T-12 (0.1) | 36 | 136 | 220 | None | None |
| Ex.2 (1.0) | (64% in DPG) | T-12 (0.2) | 31 | 106 | 155 | None | None |
| Ex.2 (1.5) | (64% in DPG) | T-12 (0.3) | 28 | 85 | 136 | None | None |
| Ex.5 (0.5) | (neat) | T-12 (0.08) | 30 | 80 | 98 | Very slight | Very slight |
| Ex.5 (1.0) | (neat) | T-12 (0.08) | 27 | 71 | 89 | None | None |
| Ex.5 (0.5) | (neat) | T-12 (0.1) | 28 | 78 | 96 | None | None |
| Ex.5 (1.0) | (neat) | T-12 (0.1) | 24 | 62 | 85 | None | None |
| Ex.5 (1.0) | (neat) | T-12 (0.2) | 20 | 53 | 77 | None | None |
| Ex.5 (1.5) | (neat) | T-12 (0.3) | 15 | 41 | 58 | None | None |
| Ex.5 (1.0) | (neat) | — | 33 | 98 | 151 | Very slight | None |
| Ex.12 (0.5) | (33% in chloro-aceto nitrile) | T-12 (0.08) | 28 | 138 | 218 | Very slight | Very slight |
| Ex.12 (1.0) | (33% in chloro-aceto nitrile) | T-12 (0.08) | 32 | 123 | 193 | None | Slight |

TABLE VI
LOW DENSITY RIGID FOAM

| Catalyst php | Solvent | Organometallic php | Cream Time Sec. | Gel Time Sec. | Tack Free Cure Time Sec. | Shrinkage | Friability |
|---|---|---|---|---|---|---|---|
| Ex.4 (0.5) | — | T-12 (0.08) | 43 | 128 | 220 | moderate-severe | slight-moderate |
| Ex.4 (1.0) | — | T-12 (0.2) | 35 | 85 | 121 | slight | slight-moderate |
| Ex.4 (1.5) | — | T-12 (0.1) | 41 | 121 | 178 | moderate | slight-moderate |
| Ex.4 (1.5) | — | T-12 (0.3) | 31 | 79 | 115 | slight | slight-moderate |
| Ex.8 (0.5) | (33% in EC) | T-12 (0.08) | 24 | 106 | 183 | OK | OK |
| Ex.8 (1.0) | (33% in EC) | T-12 (0.08) | 24 | 110 | 186 | OK | OK |

In analyzing the data for the low density polyurethane formulations, it is noted that the DAC's by themselves act as a delayed action catalyst, and to some extent, act to delay the initial catalytic effect of the tin catalyst. Although they also delay the overall reaction time, they do provide benefits in that there is little odor (musty to slight) as compared to conventional amine catalyzed polyurethane compositions and the friability and shrinkage is generally better than non-DAC containing urethanes.

It is believed that the poor shrinkage of those low density polyurethanes catalyzed by a DAC dissolved in DMF is due to the solvent itself. As is known, DMF is a solvent for the polyurethane and its presence can lead

| | |
|---|---|
| SA-1874 Polyol[4] | 15.0 |
| P-355 Polyol[5] | 5.0 |
| Water | 1.0 |
| CaCO₃ | 60 |
| R-11B Blowing Agent | 4.0 |
| Carbon Black | 1.0 |

[1]PAPI - 901 Isocyanate is crude 4,4'methylenebisphenylisocyanate which has an isocyanate equivalent of about 132 and a functionality of about 2.2.
[2]NIAX - 34–28 polyol is a polymer polyol having a molecular weight of 5000, approximately 75% primary hydroxy groups, and a hydroxyl number of about 77.2.
[3]TPE-4542 polyol is a triol having a molecular weight of about 4500 and a hydroxyl number of about 37.5.
[4]SA-1874 polyol is a cross-linking agent having a hydroxyl number of about 450. It is primarily used as a cross-linking agent.
[5]P-355 polyol is an amine-based tetrol having a hydroxyl number of about 450. It is primarily used as a cross-linking agent.

When the above semi-flexible polyurethane formulation was catalyzed with 0.1 parts bis(2-dimethylamino ethyl) ether (control) and 0.05 parts T-12 per 100 parts polyol, a cream time of 22 seconds, a gel time of 85 seconds and a cure time of 135 seconds was recorded. When the same formulation was catalyzed with 0.1 parts of Example 1 catalyst, and 0.07 parts T-12, a cream time of 34 seconds, a gel time of 98 seconds and a cure time of 135 seconds was recorded. When the same polyurethane formulation was catalyzed with 0.33 parts of Example 10 catalyst, and 0.09 parts of T-12, a cream time of 32 seconds, a gel time of 101 seconds, and a cure time of 136 seconds was recorded.

The results show that the bis(morpholino methylacetic acid) (Example 1) and the piperidino-methyl malonic acid (Example 10) catalysts are effective as a delayed action catalyst. Extended cream times were reported, but the cure time for the formulations were essentially the same as a control. What is surprising is that the level of tin in the formulation, even though substantially higher than the control, did not result in a shorter cream time than the control.

EXAMPLE 16

Conventional microcellular polyurethane foam formulations were prepared in the usual manner by mixing
 87 parts of CP-4701 polyol,
 13 parts of 1,4-butanediol,
 1.00 parts of L-5303 Silicone Surfactant and
 0.30 parts of water to form a polyol premix.
Then the tertiary amino acid (DAC) and organometallic catalyst were added and the type and concentration of each was varied as indicated.

After the catalysts were blended with the premix, 50 parts Mondur MR isocyanate were added to the premix and the resulting syrup poured into a container and evaluated as indicated in Table VIII. Terms used in the table correspond to Example 13, paragraph (5) for the high density formulations.

amine salt of a polyfunctional amino acid as represented by the formula:

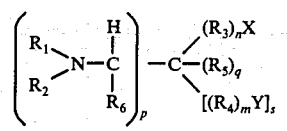

wherein $R_1$ and $R_2$ are hydrogen atoms with only one being hydrogen at a time, alkyl and substituted alkyl groups having from 1 to 15 carbon atoms, or combined to form a piperidine, piperizine, morpholine, imidazole or imidazoline radical;
wherein $R_3$ and $R_4$ are alkylene groups having from 1 to 2 atoms, aralkylene with the alkylene portion having from 2 to 6 carbons, substituted alkylene and substituted aralkylene;
wherein $R_5$ is hydrogen, a lower alkyl group having from 1 to 6 carbon atoms, an alkenyl group having from 1 to 6 carbon atoms, an aryl group, a cyclic group and substituted derivatives thereof, or a keto alkyl group with the alkyl portion having from 1 to 6 carbon atoms;
wherein $R_6$ is hydrogen, or a radical selected from the group consisting of alkyl, phenyl, furfuryl, naphthyl, and substituted derivatives of such groups;
wherein X is a carboxylic acid group or a quaternary ammonium salt of an acid group;
wherein Y is a carboxylic acid group, nitrile group, or a quaternary ammonium salt of an acid group; and
wherein $m$, $n$ and $s$ independently are 0 or 1;
wherein $q$ is 0 or 1;
wherein $p$ independently is 1 or 2; and
wherein $p + q + s$ is 3.

2. The process of claim 1 wherein said delayed action catalyst is present in a proportion of from about 0.1 to 5 parts per 100 parts of the organic compound having an active hydrogen atom.

TABLE VIII
MICROCELLULAR FOAM

| Catalyst php | Solvent | Organometallic php | Cream Time Sec. | Gel Time Sec. | Tack Free Cure Time Sec. |
|---|---|---|---|---|---|
| TEDA (0.6) | (66.6% PG) | T-12 (0.03) | 27 | 36 | 49 |
| — | (66.6% PG) | T-12 (0.2) | 28 | 39 | 54 |
| Ex.12(1.0) | (33% in $\frac{50}{50}\frac{EG}{acetonitrile}$) | T-12 (0.2) | 39 | 52 | 65 |
| Ex.12(1.0) | (33% in $\frac{50}{50}\frac{EG}{acetonitrile}$) | T-12 (0.3) | 34 | 42 | 51 |
| — | | T-12 (0.3) | 22 | 29 | 36 |
| Ex.11(1.0) | (50% DPG) | — | 272 | 400 | 600 |
| Ex.11(2.0) | (50% DPG) | — | 155 | 255 | 320 |
| Ex.11(0.5) | (50% DPG) | T-12 (0.04) | 81 | 100 | 125 |
| Ex.11(1.0) | (50% DPG) | T-12 (0.04) | 72 | 90 | 110 |
| Ex.11(2.0) | (50% DPG) | T-12 (0.04) | 71 | 90 | 105 |
| — | | T-12 (0.04) | 360+ | — | — |
| TEDA (0.6) | (67% DPG) | T-12 (0.03) | 40 | 52 | 68 |

The results for the microcellular formulation in Table VIII show that the DAC is effective for delaying the cream time of tertiary amine-tin catalyzed formulations and high tin catalyzed formulations. On the other hand, the DAC is more reactive then low tin catalyzed formulations.

What is claimed is:

1. In a process for polymerizing a urethane forming composition comprising an organic polyisocyanate and a polyol, in the presence of an organometallic catalyst, the improvement which comprises including as a catalyst component an amino catalyst selected from the group consisting of a polyfunctional amino acid and an 3. The process of claim 2 wherein from about 0.005 to 0.5 parts of an organometallic catalyst per 100 parts polyol are included.

4. The process of claim 1 wherein the organometallic catalyst is an organo tin compound.

5. The process of claim 4 wherein $s$ in the formula is 1.

6. The process of claim 5 wherein Y in the formula is a carboxylic acid group.

7. The process of claim 4 wherein $R_1$ and $R_2$ in the formula are selected from the group consisting of lower alkanol groups having from 2 to 4 carbon atoms, and lower alkyl groups having from 1 to 3 carbon atoms, or are combined to form a morpholino, imidazolo, or piperidinyl group.

8. The process of claim 5 wherein $n$ and $m$ in the formula are 0.

9. The process of claim 5 wherein $R_5$ is hydrogen, Q is 1, and $R_6$ in the formula is a phenyl group.

10. The process of claim 9 wherein $R_6$ in the formula is hydrogen.

11. In a process for polymerizing a urethane forming composition comprising a polyisocyanate and polyol in the presence of from about 0.005 to about 0.5 parts of an organo tin catalyst per 100 parts polyol, the improvement which comprises including from about 0.1 to about 5 parts of an amino catalyst per 100 parts polyol, the amino catalyst being a Mannich Adduct reaction product of a secondary amine selected from the group consisting of lower alkanol amnines with the alkanol portion having from 2-4 carbon atoms, morpholine, piperidine and imidazole; an aldehyde selected from the group consisting of formaldehyde and benzaldehyde; and malonic acid.

* * * * *